Figure 1:
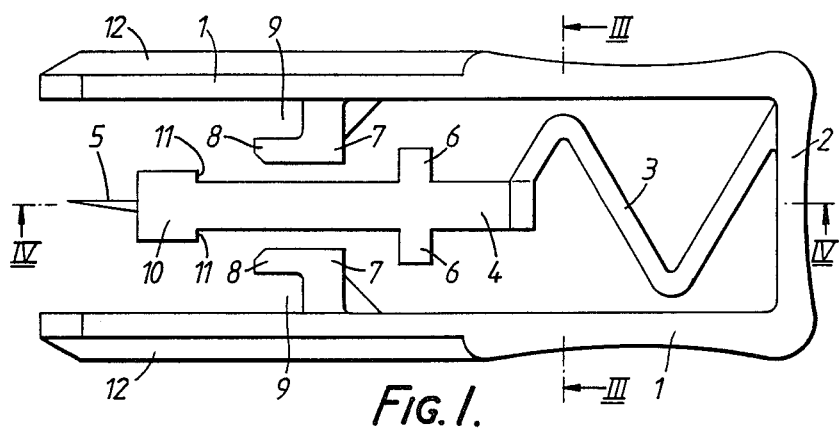

United States Patent [19]
Crossman et al.

[11] Patent Number: 4,869,249
[45] Date of Patent: Sep. 26, 1989

[54] BLOOD SAMPLING DEVICES

[75] Inventors: David D. Crossman, Watlington; Ernest J. Mumford, Witney; Jeremy Marshall, Newington, all of United Kingdom

[73] Assignee: Owen Mumford Limited, Woodstock, United Kingdom

[21] Appl. No.: 189,691

[22] Filed: May 2, 1988

[30] Foreign Application Priority Data

May 1, 1987 [GB] United Kingdom ................. 8710470

[51] Int. Cl.$^4$ ............................................ A61B 27/34
[52] U.S. Cl. ................................ 128/314; 128/329 R
[58] Field of Search ................... 128/314, 315, 329 R, 128/763, 770

[56] References Cited

U.S. PATENT DOCUMENTS

| | | | |
|---|---|---|---|
| 3,030,959 | 4/1962 | Grunert | 128/314 X |
| 4,449,529 | 5/1984 | Burns et al. | 128/314 |
| 4,452,243 | 6/1984 | Leopoldi et al. | 128/314 |

Primary Examiner—Michael H. Thaler
Attorney, Agent, or Firm—Young & Thompson

[57] ABSTRACT

A disposable pricker has a body (1,2) lance (4) spring (3) and cap (13) integrally moulded in plastics, the cap being subsequently separable. The lance tip (5) is a needle embedded in the moulding and relatively inaccessible within the body. Formations (17) within the cap compress the spring (3) as the cap is fitted until they are flexed aside by co-operation with abutments (7) within the body. The lance (4) is released and shoots forward for the tip (5) momentarily to project proud of the cap (13). The latter is made captive to the lance (4) during this movement and cannot be removed to repeat the operation. The lance tip (5) thus remains concealed within the cap (13). In another capless version, squeezing the body (31) wedges the lance (36) back until it escapes and is shot forward by a spring (38). On recovery within the body, the lance is blocked from reverting to the position where it can be re-actuated.

5 Claims, 3 Drawing Sheets

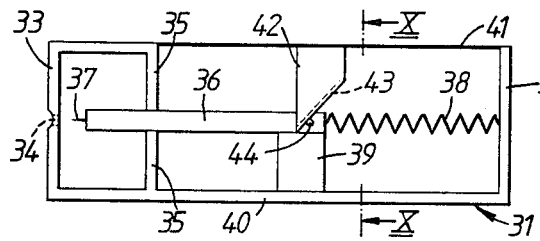
FIG.9.a
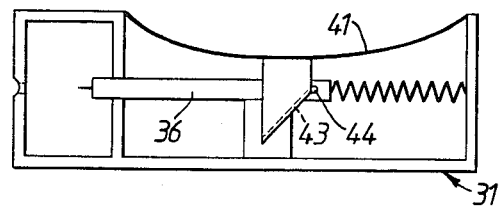
FIG.9.b
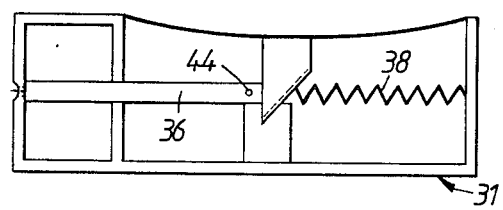
FIG.9.c
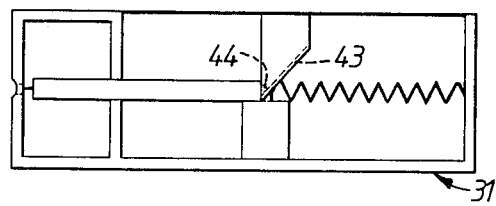
FIG.9.d
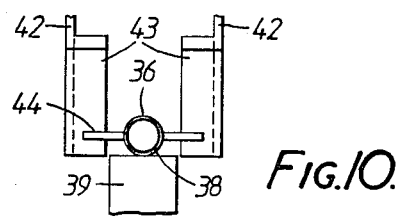
FIG.10.

BLOOD SAMPLING DEVICES

This invention relates to blood sampling devices, and in particular to a pricker to draw a small drop of blood for analysis. Such prickers are widely used by diabetics, for example, who need to know their sugar level. However, there are many other applications.

These days, with AIDS, there is widespread concern surrounding the use of needles and their part in transmitting disease. Once a needle has been used on an infected person, subsequent use or an accidental prick on another could be fatal.

There is therefore likely to be a growing demand for a pricker which can be used just once and, having been used, be rendered safe for carriage and disposal. It is the aim of this invention to provide such an instrument.

According to the present invention there is provided a disposable pricker comprising a body with a spring-loaded lance carried therein, the lance tip normally being in a retracted position but on energisation and release of the spring means having a momentary projecting position, and means for co-operation with the lance to prevent re-energisation and further momentary projection.

In the preferred arrangement, the body has a cap which provides a passage through which the lance tip can move, the fitting of the cap energising the spring means and then releasing the lance to cause the momentary projection of the tip through the cap, the prevention means being catch means holding the cap to the body with the tip within said passage.

During fitting of the cap the lance may be arranged to co-operate with a first part of a formation inside the cap, and a second part of this formation may be arranged to co-operate with an abutment within the body, the fitting of the cap causing the first part to push the lance further back into the body against its spring-loading, until the second part is engaged by the abutment which causes the formation to flex and the first part to release the lance.

The lance may be anchored by its spring-loading to the body. The catch means may then comprise a third part of said formation and a portion on the lance which is sprung past said third part after release of the lance.

In an alternative arrangement the body is deformable, as by squeezing, such deformation being arranged to energise the spring means and then release the lance to cause the momentary projection of the tip. The body when recovering and released from said deformation provides an obstruction to the full recovery of the lance, whereby it is prevented from being reactuated.

Preferably, there will be stop means to limit the forward thrust of the lance, and with the cap version this may be provided by the abutment and a further portion of the lance.

Conveniently, the body, spring means and lance are integrally moulded in plastics material, the lance tip being a needle embedded in said moulding. The cap may also be integrally moulded with the body, being breakably joined thereto by a weak bridge.

Figure 2:
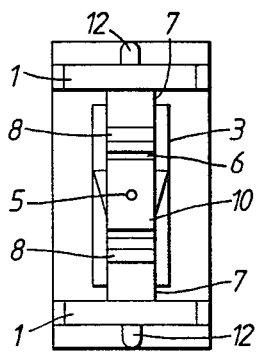
Figure 3:
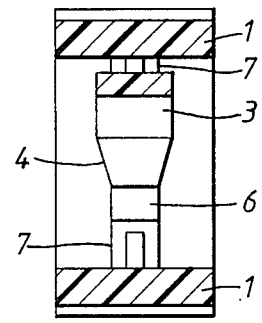
Figure 4:
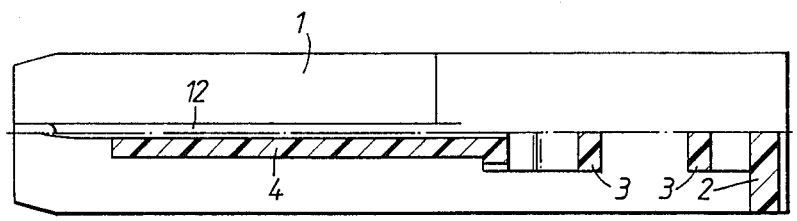
Figure 5:
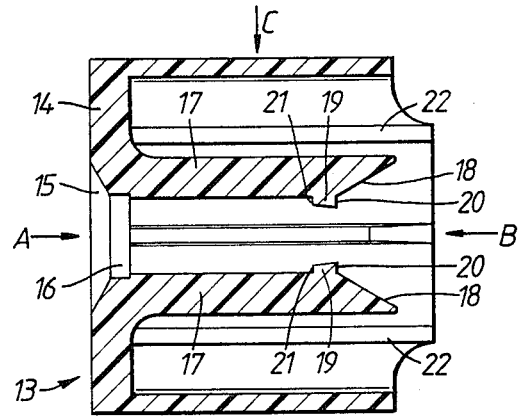
Figure 6:
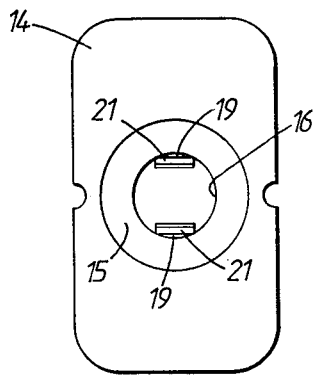
Figure 7:
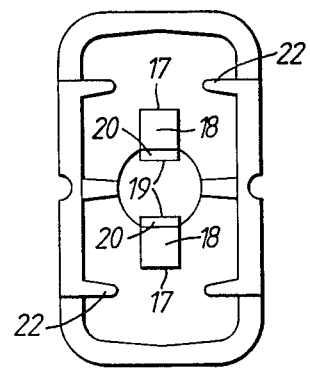
Figure 8:
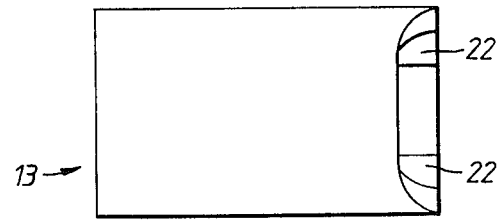
Figure 11:
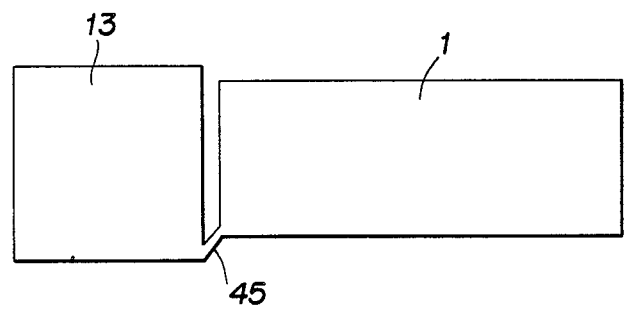

For a better understanding of the invention, one embodiment will now be described, by way of example, with reference to the accompanying drawings, in which:

FIG. 1 is a side view of the body of a pricker,
FIG. 2 is an end view of the pricker body of FIG. 1,
FIG. 3 is a section on the line III—III of FIG. 1,
FIG. 4 is a part section on the line IV—IV of FIG. 1,
FIG. 5 is a longitudinal section of a cap for the pricker body,
FIG. 6 is an end view in the direction A of the cap of FIG. 5,
FIG. 7 is an end vie in the direction B of the cap of FIG. 5,
FIG. 8 is a plan view in the direction C of the pricker cap.
FIGS. 9(a)-9(d) show diagrammatic side views of an alternative pricker, in sequence of operation.
FIG. 10 is a cross-section on the line X—X of FIG. 9(a).
FIG. 11 is a diagrammatic plan view of the pricker body of FIGS. 1-4 and the cap of FIGS. 5-8, moulded together.

The body of FIGS. 1 to 4 is generally U-shaped with two parallel arms 1 joined by a web 2. A spring 3 of bent strip form zigzags from the inside of the web 2 towards the mouth of the U and carries at its end a lance 4, this being integrally moulded in plastics with the spring and body. Polypropylene is a suitable material to provide the required resilience. The free or forward end of the lance has a sharp needle 5 embedded therein, its tip being slightly retracted within the mouth of the U in the relaxed state of the spring 3.

Towards its rear end, the lance 4 has two opposed lugs 6 projecting towards the respective arms 1, while further towards the mouth of the U, the arms have inwardly projecting abutments 7. The rear faces of these provide stops against which the lugs 6 hit when the spring is released after being compressed in a pricking operation, as described below. On the other side, towards the mouth of the U, the abutments 7 have forwardly extending projections 8 spaced from the arms to provide indents 9.

The lance has an enlargement 10 at its forward end providing rearwardly facing shoulders 11, but it is sufficiently small to pass freely between the abutments 7 when the spring is compressed.

Externally, the body has a tapered leading end to both arms 1 and along the centre of each of these there runs a guide rib 12, for just over half the length. Thereafter the outside of each arm is slightly indented, as is the web 2, for ease and comfort of handling.

Referring now to FIGS. 5 to 8, the cap 13 is a cup-like structure of generally rectangular section. Its base 14 has a central aperture 15 which is coned before leading into a cylindrical portion 16. This is where the thumb or finger is placed to be pricked. On opposite sides of this aperture, integrally moulded within the cap, there are fingers 17 extending parallel to the sides almost to the mouth of the cap. At their free ends the fingers 17 have outwardly flared internal surfaces 18, and where each of these joins the main length of the finger there is a lug 19 providing an outer shoulder 20 and an inner shoulder 21. The mutually facing surfaces of these lugs are sloped to be convergent towards the mouth of the cap.

On the inside of the larger side walls of the cap 13 there are longitudinal guide ribs 22 which engage inside the edge portions of the arms 1 to keep the latter parallel as the body and cap are brought together, while each rib 12 slides in the apex of the very shallow interior V-shape of the associated smaller side wall.

While the body and the cap have been described as being separate entities, they can in fact both be moulded together, with a short breakable bridge 45 between them, as shown in FIG. 11. Preferably, the cap will even then be over the mouth of the U, giving some protection to the needle 5, but differently oriented for ease of moulding. After manufacture, the whole assembly will be packaged and may be subjected to radiation to sterilise the needle.

For use, the cap will be removed, if attached to the body, and then offered up again to slide over the mouth of the U. Before it has gone very far, the shoulders 20 will engage the front of the lance 4, and as the cap is pressed further on so the lance is pushed back, compressing the spring 3. After further travel, the flared surfaces 18 of the fingers 17 engage the projections 8 and, as the cap is urged further over the body, so the fingers 17 are spread apart, the tips entering the indents 9. At this point, the user will be pressing a finger or thumb into the aperture 15 so that a bulge projects into the cylindrical portion 16. A final push compressing the cap and body together causes the lugs 19 to be spread clear of the enlargement 10 and, since the spring 3 is now fully compressed, the lance shoots forward. Its travel is limited by the lugs 6 engaging the abutments 7, but this is just sufficient for the needle 5 to enter the cylindrical portion 16 and break the skin. This is only momentary since the spring 3 then withdraws the lance and it rapidly damps down into its initial position.

When mutual pressure between cap and body is relieved, the flared surfaces 18 acting on the projections 8 wedge the cap back so that the fingers 17 close parallel to one another again. The shoulders 11 will then be beyond the lugs 19 in the direction of the aperture 15 and so any attempt subsequently to remove the cap is prevented by abutment of the shoulders 11 and 21. The cap may slide back and forth but the needle 5 will remain safely concealed within it. Pulling the cap will merely extend the spring 3, while pushing it will be limited by the forward ends of the arms 1 engaging the base 14 of the cap 3. The latter cannot recompress the spring to cause it to shoot the needle forward again. The device can therefore be carried around safely after use, and be disposed of without special precautions.

In the alternative arrangement of FIGS. 9 and 10, no cap is required. The body 31 is elongated and generally rectangular in side view with a closed rear end 32 and a forward end 33 with an aperture 34. A short distance behind this forward end wall there are guides 35 for a lance 36 whose tip 37 can enter the aperture 34 momentarily in a manner similar to that of the previous embodiment. A spring 38 acts between the rear end of the lance 36 and the wall 32 and in its relaxed condition the position is as shown in FIG. 9(a) with the lance tip 37 set back from the aperture 34.

The rear end of the lance 36 rests on a support 39 projecting inwardly from one longitudinal wall 40. The opposite wall 41, which is thinner and resiliently flexible, has two cheeks 42 projecting inwardly opposite the support 39, one to each side as best seen in FIG. 10. The inner ends of these cheeks slope from their forward ends back towards the wall 41 and have inturned flanges 43. A pin 44 transversely through the rear end of the lance 36 co-operates with these flanges and in the initial position of FIG. 9(a) the ends of the pin bear against the ends of the flanges near the tips of the cheeks 42 and on the sides facing to the rear. The overall length of the pin 44 is less than the spacing between the cheeks.

To operate the pricker, the end 33 is held against the skin and the body 31 is squeezed, deforming the wall 41 inwardly as shown in FIG. 9(b). The flanges 43 wedge the pin 44, and thus the lance 36, rearwardly. At the extremity of this movement, the pin 44 reaches the outer ends of the flanges 43 and escapes, the spring 38 then shooting the lance 36 forwards to prick the skin as shown in FIG. 9(c). The leading end of the lance is stopped by abutting the forward end 33 around the aperture 34. The lance retracts, towards the FIG. 9(d) position, but the pin 44 is now obstructed by the forward sides of the flanges 43 and cannot recover to the rear sides where the pricker could be actuated again.

We claim:

1. A disposable pricker comprising a body, a lance, spring means acting between the lance and the body so that in a relaxed condition of the spring means the lance is in a first retracted position within the body, a cap for the body providing a passing through which the lance tip can move, a formation within the cap for engaging the lance and urging it to a second retracted position, thereby energizing the spring means, as the cap is fitted, means within the body to engage the cap formation as fitting is completed thereby to release the lance, enabling the spring means to cause momentary projection of the lance tip from the passage, and catch means holding the cap to the body when fitting is completed with the lance tip within the passage.

2. A pricker as claimed in claim 1, wherein the cap is integrally moulded with the body, spring means, and lance, the lance tip being a needle embedded in said moulding, and wherein the cap is breakably joined to the body by a weak bridge.

3. A pricker as claimed in claim 1, wherein the cap formation is resiliently flexible and the means within the body comprises an abutment which cause the formation to flex as it engages that abutment.

4. A pricker as claimed in claim 3, wherein the lance is anchored by the spring means to the body and wherein the catch means comprise part of said cap formation and a portion on the lance which is sprung past said part after release of the lance.

5. A pricker as claimed in claim 3, wherein said abutment and a further portion of said lance provide stop means to limit the forward thrust of the lance.

* * * * *